United States Patent [19]
Allen

[11] Patent Number: 5,507,794
[45] Date of Patent: Apr. 16, 1996

[54] THERAPEUTIC SUPPORT GARMENT

[76] Inventor: Patricia A. Allen, P.O. Box 3726, Hayward, Calif. 94541

[21] Appl. No.: 369,787

[22] Filed: Jan. 6, 1995

[51] Int. Cl.⁶ ...................................... A61F 7/00
[52] U.S. Cl. .................... 607/112; 607/114; 126/204; 62/530
[58] Field of Search .................... 607/108, 112, 607/114; 383/901; 126/204; 165/46; 62/530

[56] References Cited

U.S. PATENT DOCUMENTS

| | | | |
|---|---|---|---|
| 4,676,247 | 6/1987 | Van Cleve | 607/112 |
| 5,050,595 | 9/1991 | Krafft | 607/108 |
| 5,215,080 | 6/1993 | Thomas et al. | 607/112 |
| 5,235,974 | 8/1993 | Miller | 607/108 |
| 5,304,215 | 4/1994 | MacWhinnie et al. | |

Primary Examiner—Angela D. Sykes
Assistant Examiner—Robert L. Nasser, Jr.
Attorney, Agent, or Firm—Ralph C. Francis

[57] ABSTRACT

Disclosed herein is a therapeutic support garment comprising an elongated support member having two ends, an adjustable securing member for removably securing the support member ends, at least one breast pouch disposed on the support member, a positioning member for removably positioning the breast pouch, and a temperature regulator positioned in the breast pouch for imparting a predetermined temperature to the wearer's breast regions to relieve the discomforts of swelling and tenderness thereof.

11 Claims, 3 Drawing Sheets

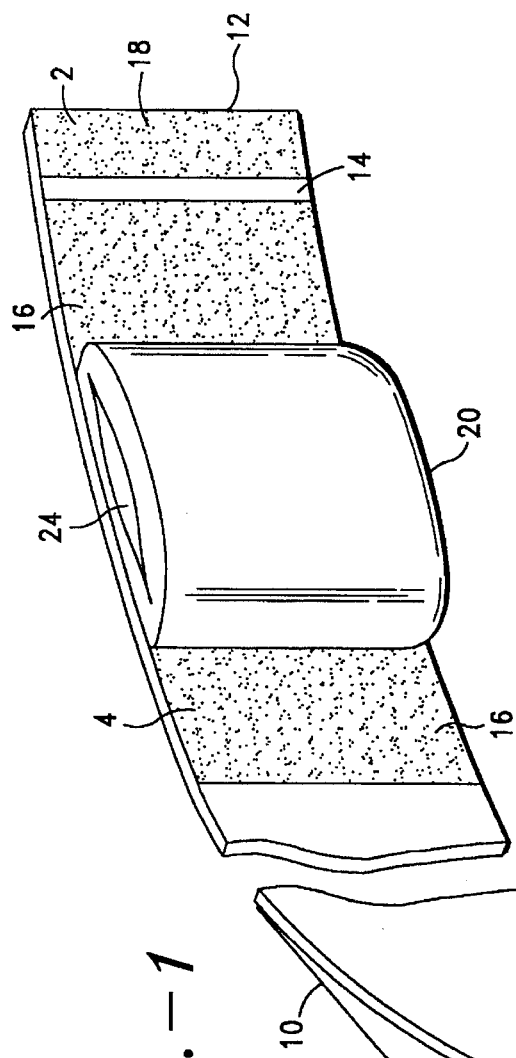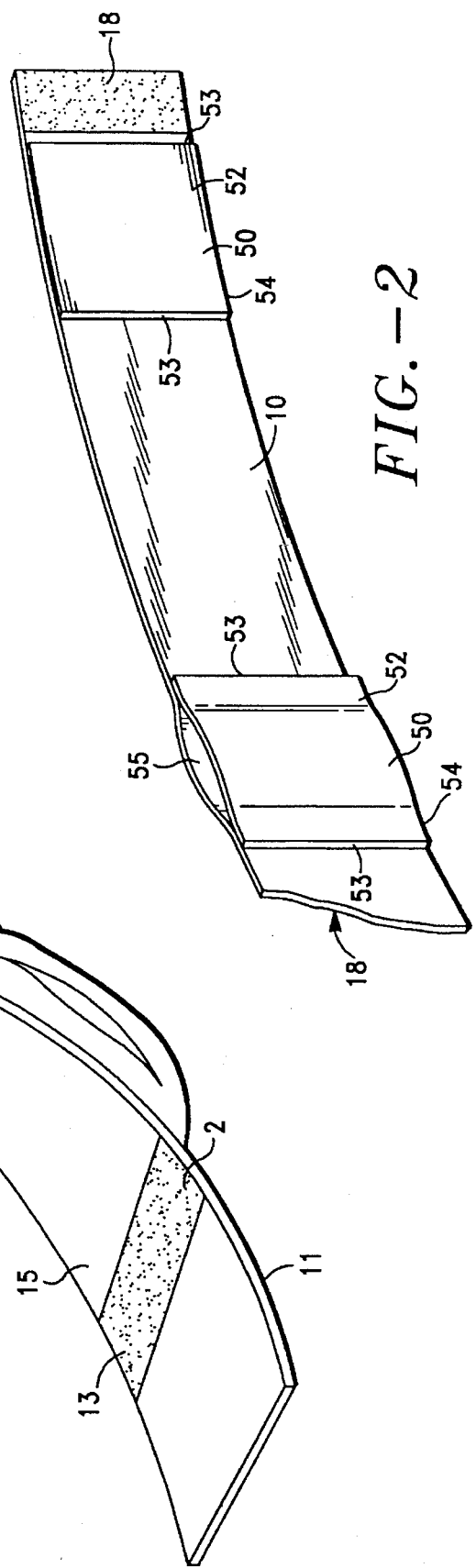

THERAPEUTIC SUPPORT GARMENT

FIELD OF THE INVENTION

This invention relates generally to therapeutic support garments. More particularly, the invention relates to a therapeutic support garment which readily conforms to the contours of different sized female breasts to provide therapeutic heat or cold to an adjacent breast region to reduce swelling and irritation.

BACKGROUND OF THE INVENTION

During the premenstrual period, pregnancy and the post-partum period, most women suffer the discomforts of swelling (i.e. engorgement) and tenderness of the breasts, nipples and surrounding tissues due to fluid retention or lactation. To alleviate the pain and/or discomfort associated with breast engorgement, doctors generally recommend the application of moist heat (e.g., water compresses, hot showers) to relieve tenderness or cold compresses to reduce swelling. This is, of course, very inconvenient and, in many instances, impractical for a busy nursing mother.

Various thermal heat packs have been employed to provide therapeutic heat to the human body. However, heat packs have many disadvantages. Most significantly, the devices generally include cup shaped portions which do not conform closely to various sizes of the breasts, resulting in uneven application of heat to the breast. Illustrative are the heat packs disclosed in U.S. Pat. Nos. Re: 14,024, 2,298,361, 3,500,832, 5,050,595 and 5,304,215.

A brassiere capable of providing gentle support of the breast tissues can also help relieve the discomforts associated with breast engorgement. However, brassieres tend to provide an uneven pressure on delicate tissue and can cause greater complications. Illustrative is the brassiere disclosed in U.S. Pat. No. 5,050,595.

The brassiere disclosed in the above noted patent comprises a pair of breast supporting cups, each with a thermal gel pack placed therein. Although the brassiere facilitates heating or cooling of the breasts, the device has many disadvantages, which include (i) uneven temperature and pressure distribution to a woman's breast region and (ii) limited areas of heating or cooling.

Further, the brassiere requires a multitude of sizes to accommodate the wide range of female breast sizes and shapes. Consequently, it is necessary to provide various sizes of gel packs for the multitude of brassiere sizes.

Therefore, what is needed is a support garment which is capable of providing uniform pressure and therapeutic heat or cold to the breast and adjacent areas to relieve the discomforts of swelling and tenderness in the breast regions.

SUMMARY OF THE INVENTION

It is an object of this invention to provide a simple, pliable, lightweight therapeutic support garment which readily conforms to the contours of any size female breast to provide therapeutic heat or cold to the adjacent breast region.

It is an additional object of this invention to provide such a support garment with adjustable breast pouches to accommodate a wide range of breast sizes and configurations.

It is an additional object of this invention to provide such a support garment which provides an even distribution of temperature and pressure about the breast region.

In accordance with the above objects and those that will be mentioned and will become apparent below, the therapeutic support garment in accordance with this invention comprises:

An elongated support member having two ends, a securing member for removably securing the support member ends, a breast pouch disposed on the support member, and a temperature regulator positioned in the breast pouch for imparting a predetermined temperature, whereby when the support garment is positioned about the upper torso of the wearer heat or cold is applied immediately adjacent said breast pouch.

In a preferred embodiment, the support garment includes a plurality of removable breast pouches and positioning means for positioning the breast pouches on the support member. The adjustable breast pouches facilitate the heating and cooling of (i) various breast sizes and shapes and (ii) adjacent breast regions, including the axillary region.

Thus, the advantages of the present invention are as follows: The therapeutic support garment (i) readily conforms to the contours of the breast regions to provide an even distribution of therapeutic heat or cold, (ii) accommodates a wide range of breast sizes and shapes, and (iii) provides an even distribution of pressure to the breast regions.

BRIEF DESCRIPTION OF THE DRAWINGS

For a further understanding of the objects and advantages of the present invention, reference should be had to the following detailed description, taken in conjunction with the accompanying drawings, in which like parts are given like reference numerals and wherein:

FIG. 1 is a perspective view of a therapeutic support garment according to the invention;

FIG. 2 is a perspective view of a further embodiment of the therapeutic support garment;

DETAILED DESCRIPTION OF THE INVENTION

Figure 3:
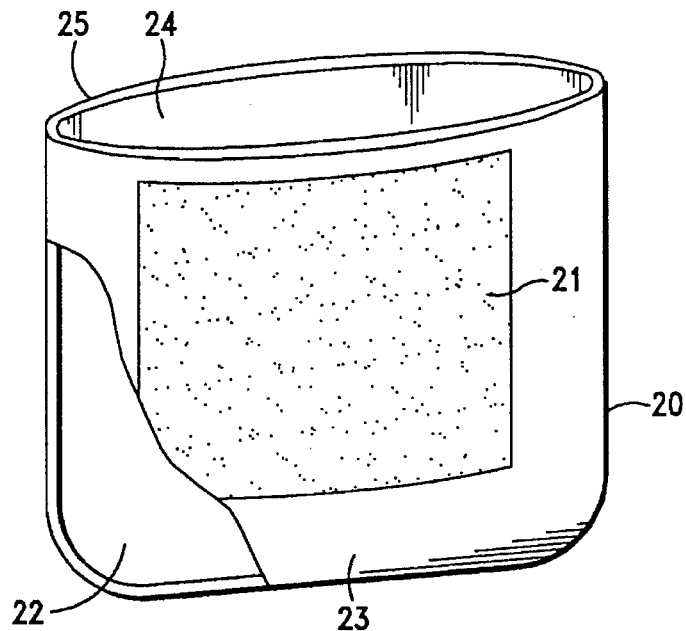
FIG. 3 is a perspective view of a breast pouch according to the invention.

FIG. 1 illustrates, in simplified form, a therapeutic support garment according to the present invention. In a preferred embodiment, the support garment includes an elongated support member 10 and a pair of breast pouches 20. The support member 10 is preferably wide enough to cover the wearer's breast regions and long enough to accommodate a wide range of upper torso sizes in conjunction with the adjustable securing member, discussed below. By the term "breast region" it is meant to include the breast (or mammary gland) and related chest wall, aereolae, nipple and axillary region.

Although the fabric used to construct the elongated support member 10 according to the invention may be selected from a variety of materials, it is preferred to employ a soft, flexible, elastic material which is capable of stretching in multiple directions. Examples of such materials are Lycra®, Spandex and Nylon. A support garment made of the noted materials will apply pressure more evenly against the wearer's upper torso for maximum therapeutic effect and comfort.

As illustrated in FIG. 1, the elongated support member 10 includes an adjustable securing member 2 for removably securing the support member ends 11, 12. The securing member 2 is adapted to accommodate a wide range of upper torso sizes while providing substantially even pressure about the wearer's breast regions. As will be recognized in the art, various adjustable securing members may be employed to achieve the adjustable tensioning of the invention, such as a plurality of appropriately positioned conventional snaps, buttons and hooks.

In a preferred embodiment, the adjustable securing member 2 includes a layer 13 of hook-like material disposed proximate one end 11 of the support member 10 on one side thereof 15. A layer 18 of fibrous material is also disposed proximate the opposite end 12 of the support member 10 on the opposite side (i.e. inside surface) thereof 14. The hook-like material in layer 13 is operable to mesh with the fibrous material in layer 18 to form an adjustable attachment therefor. This type of cooperating material is commonly referred to under the trade name Velcro®.

Figure 6:
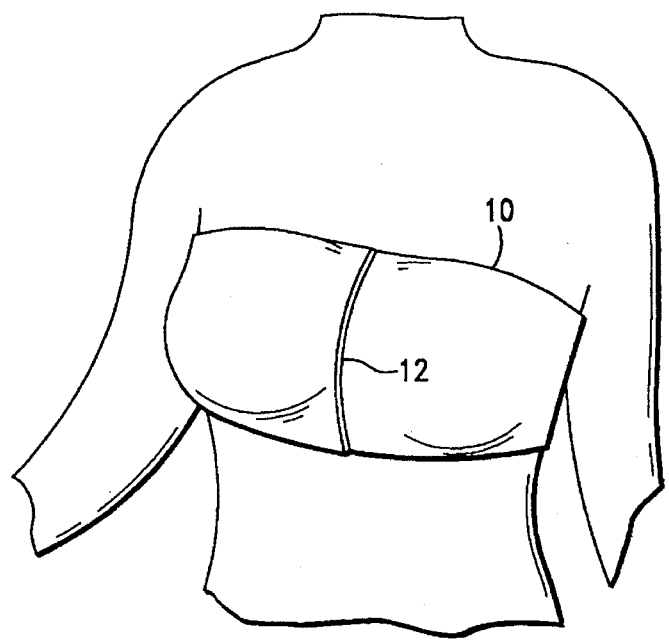
FIG. 6 illustrates the therapeutic support garment shown in FIG. 1 about the upper torso of a wearer.

Thus, as the support member 10 is wrapped around the upper torso of the wearer, the two overlapping ends 11, 12 are positioned accordingly to achieve an even distribution of pressure about the wearer's breast regions. (See FIG. 6.) As will be recognized by one ordinarily skilled in the art, the adjustable securing member 2 of the invention will accommodate a wide range of breast sizes and configurations. This eliminates the need for multiple band sizes and cups as is generally required with conventional brassieres.

As discussed above, a key feature of the invention is the positioning member 4 for removably positioning the breast pouches 20 on the support member 10. The positioning member 4 thus facilitates the heating and cooling of (i) various breast sizes and shapes, and (ii) adjacent breast regions, including the axillary region. In a preferred embodiment of the invention, the positioning member 4 also includes a layer 16 of fibrous material. As illustrated in FIGS. 1 and 3, the fibrous layer 16 is generally disposed over a substantial portion of the inside surface 14 of the elongated support member 10 to facilitate a wide range of breast pouch 20 positions. A layer 21 of hook-like material is also disposed on one side 23 of each breast pouch 20 to facilitate attachment to and positioning of the breast pouches 20 on the support member 10.

Alternatively, the positioning member 4 can comprise a plurality of appropriately positioned snaps, buttons and hooks. As will be recognized by one of ordinary skill in the art, the support member 10 of the invention is adapted to accommodate a wide range of alternative positioning members.

Figure 4:
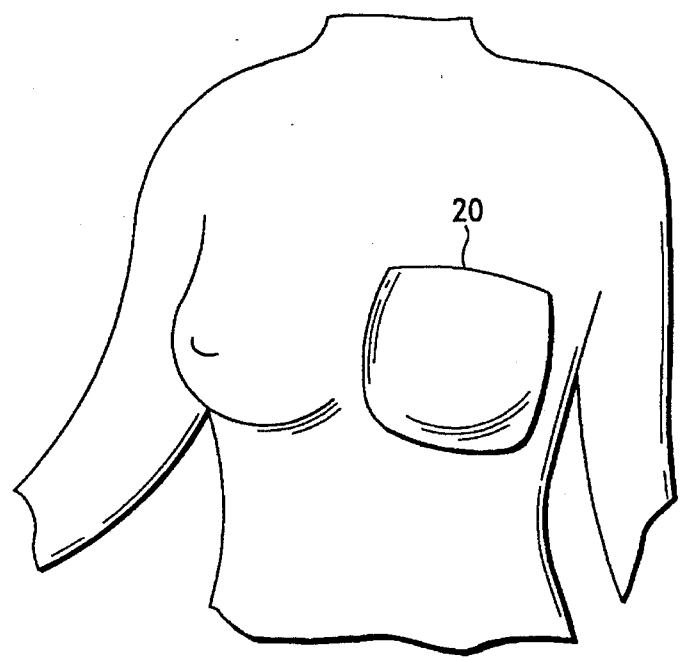
FIG. 4 is a plan view of a breast pouch positioned on a female breast according to the invention.

Referring to FIG. 4, the breast pouches 20 of the invention are designed and configured to accommodate a wide range of breast sizes. According to the invention, each breast pouch 20 is large enough to cover a wearer's breast region. Preferably, the breast pouches 20 are approximately 6 inches wide by 6 inches long.

The breast pouches 20 are preferably composed of a soft, heat-conductive material such as terry cloth or brushed cotton. Of course, other materials, such as Lycra®, nylon and poly-wool blends, can also be used within the scope of this invention.

According to the invention, as illustrated in FIG. 3, each breast pouch 20 includes an enclosure 22 and an opening 24 communicating with the enclosure 22. The opening 24 is dimensioned and configured to allow the disposable temperature regulator 40 (discussed below) to be inserted through the opening 24 and positioned in the breast pouch enclosure 22. The breast pouches 20 can also include securing means, such as Velcro®, snaps or buttons, disposed proximate the opening edge 25, to secure the temperature regulator 40 in the breast pouch enclosure 22.

Figure 5:
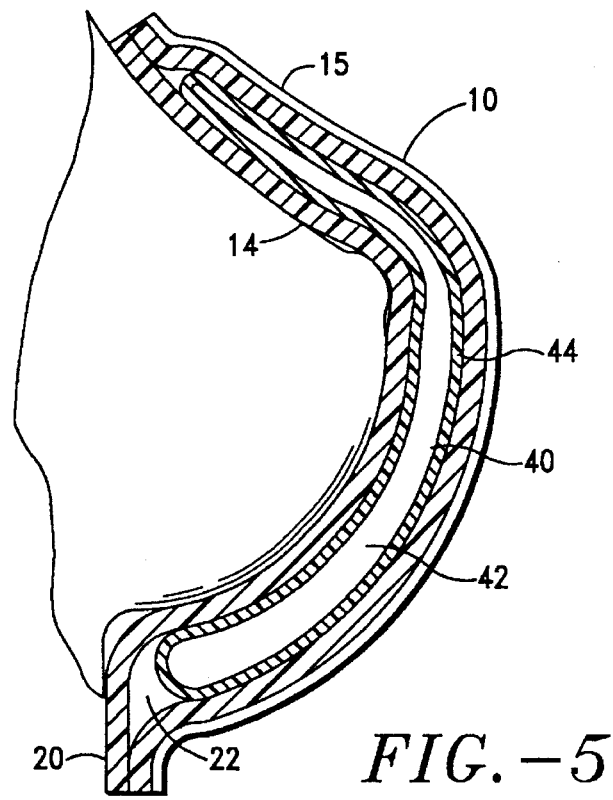
FIG. 5 is a cross-sectional view of a breast pouch employed in the therapeutic support garment shown in FIG. 1.

Referring to FIG. 5, the temperature regulator 40 is positioned in the breast pouch enclosure 22 and configured to envelope the wearer's breast region. In a preferred embodiment, the temperature regulator 40 comprises a conventional thermal gel pack. The gel pack 40 includes a temperature retaining gelatinous medium 42 enclosed within a heat conducting envelope 44. Typically, the envelope 44 is composed of a flexible plastic film such as polyethylene.

The gel packs 40 may be heated or cooled by conventional means, such as a microwave oven or conventional refrigeration. Although the optimal heating and cooling temperature ranges to achieve maximum therapeutic effect varies with the individual, the inventor has found that the following ranges generally achieve superior therapeutic effects: Heating 105° C. to 115° C.; Cooling 32° to °C. The gel packs 40 should also have the capacity to retain the desired temperature over an extended period of time, preferably, $\leq 1°$ C./min.

The heat or cold from the gel packs 40 when positioned in the breast pouches 20 reduces swelling and tenderness of the breast tissues and relieves the discomforts occurring during a woman's premenstrual period, pregnancy and/or the post-partum period. Additionally, due to the unique design and configuration of the invention, the therapeutic support garment may be employed to relieve the discomforts associated with various surgical procedures, such as breast biopsy, lumpectomy, a mastectomy or heart surgery.

Referring to FIG. 2, there is shown an additional embodiment of the invention wherein the breast pouches 50 are permanently positioned and secured on the support member 10. In this embodiment, the breast pouches 50 comprise a pair of inner panels 52 secured on the side 53 and bottom 54 edges by conventional means. The panels 52 and support member 10 form between them pockets 55 for receiving the temperature regulator 40.

In additional embodiments of the invention, not shown, an adjustable tie strap may be employed. The tie strap would provide additional support to the woman's breasts to enhance comfort.

Without departing from the spirit and scope of this invention, one of ordinary skill may make various changes and modifications to the invention to adapt it to various usages and conditions. As such, these changes and modifications are properly, equitably and intended to be, within the full range of equivalence of the following claims.

What is claimed is:

1. A therapeutic support garment kit dimensioned and configured to encircle the upper torso of a wearer, comprising:

an elongated elastic support member having two ends;

a securing member for removably securing said support member ends;

a plurality of breast pouches, each being selectively attachable and detachable to said support member, wherein each breast pouch is of a different size, and wherein at least one of said pouches is attachable to said support member at any given time;

a thermal pack disposed in said breast pouch for imparting a predetermined temperature, whereby when said support member is positioned about the upper torso of the wearer, heat or cold is applied immediately adjacent said breast pouch.

2. The support garment as set forth in claim 1, wherein said securing member is adjustable to selectively provide a substantially even pressure about the wearer's breast regions.

3. The support garment as set forth in claim 1, wherein said thermal pack is disposable.

4. The support garment as set forth in claim 1, wherein the breast pouch is composed of a heat conductive material.

5. A therapeutic support garment kit dimensioned and configured to encircle the upper torso of a wearer, comprising:

an elongate elastic support member having two ends, an adjustable securing mechanism disposed on said support member ends;

a plurality of interchangeable breast pouch kits, each kit including multiple breast pouches having an enclosure therein, said breast pouches being selectively attachable and detachable to said support member, wherein each kit includes different sized pouches;

a positioning member for removably positioning said breast pouches on said support member;

a thermal pack disposed in each of said breast pouches for imparting a predetermined temperature to the wearer's breast regions, whereby when said support member is positioned about the upper torso of the wearer, heat or cold is immediately applied adjacent said breast pouches.

6. The support garment as set forth in claim 5, wherein said support member is wide enough to cover the wearer's breast regions.

7. The support garment as set forth in claim 5, wherein said breast pouches are substantially cup shaped.

8. The support garment as set forth in claim 7, wherein said breast pouches are composed of a soft, heat-conductive material.

9. The support garment as set forth in claim 5, wherein each of said breast pouches includes an opening communicating with said breast pouch enclosure, said opening being dimensioned and configured to allow said thermal pack to be inserted through said opening and positioned in each of said breast pouch enclosures.

10. The support garment as set forth in claim 5, wherein said thermal pack is disposable.

11. The support garment as set forth in claim 10, wherein said thermal pack comprises a thermal gel pack.

* * * * *